United States Patent
Tripathi et al.

[19]
[11] Patent Number: 6,085,582
[45] Date of Patent: Jul. 11, 2000

[54] VEHICLE MASS EMISSION MEASUREMENT

[75] Inventors: Pradeep R. Tripathi, Ypsilanti; Gideon Eden, Ann Arbor; Donald M. Soenen, Saline; Carl D. Ensfield, Dexter; Harold M. Ryan, Pinckney; Robert K. Zummer, Ann Arbor, all of Mich.

[73] Assignee: Sensors, Inc., Saline, Mich.

[21] Appl. No.: 09/069,551

[22] Filed: Apr. 29, 1998

Related U.S. Application Data

[60] Provisional application No. 60/047,192, May 20, 1997.

[51] Int. Cl.⁷ .................................................. G01M 19/00
[52] U.S. Cl. .......................... 73/118.1; 73/116; 73/23.31; 73/23.32
[58] Field of Search ................................. 73/23.31, 23.32, 73/118.1, 116, 23, 28, 863.41

[56] References Cited

U.S. PATENT DOCUMENTS

| | | |
|---|---|---|
| 3,593,023 | 7/1971 | Dodson et al. |
| 3,603,155 | 9/1971 | Morris et al. |
| 3,696,247 | 10/1972 | McIntosh et al. |
| 4,160,373 | 7/1979 | Fastaia et al. |
| 4,341,108 | 7/1982 | Warncke et al. |
| 4,586,367 | 5/1986 | Lewis . |
| 4,660,408 | 4/1987 | Lewis . |
| 4,727,746 | 3/1988 | Mikasa et al. |
| 4,823,591 | 4/1989 | Lewis . |
| 5,129,257 | 7/1992 | Carduner et al. |
| 5,184,501 | 2/1993 | Lewis et al. |
| 5,218,857 | 6/1993 | Decker et al. |
| 5,337,595 | 8/1994 | Lewis . |
| 5,357,113 | 10/1994 | Liston et al. |
| 5,419,178 | 5/1995 | Decker et al. |
| 5,423,228 | 6/1995 | Budd et al. |
| 5,469,731 | 11/1995 | Decker et al. |
| 5,526,122 | 6/1996 | Intemann et al. |
| 5,546,788 | 8/1996 | Dickow . |
| 5,569,838 | 10/1996 | Broedel et al. |
| 5,591,406 | 1/1997 | Hirai et al. ............................. 73/23.36 |
| 5,596,154 | 1/1997 | Baughman . |
| 5,621,166 | 4/1997 | Butler . |
| 5,639,957 | 6/1997 | Zarchy . |
| 5,739,413 | 4/1998 | Kohn et al. |
| 5,929,320 | 7/1999 | Yoo ...................................... 73/23.31 |

FOREIGN PATENT DOCUMENTS

| | | |
|---|---|---|
| 0414446 A2 | 2/1991 | European Pat. Off. |
| 0501242 A1 | 9/1992 | European Pat. Off. |
| 3923737 C2 | 12/1995 | Germany . |

OTHER PUBLICATIONS

Search Report from corresponding European Patent Application No. EP 98650027.0. Jan. 12, 1998.

Bureau of Mobile Sources, "New York State Department of Enviromental Conservation, New York Metropolitan Area Enhanced Inspection/Maintenance Program, Technical Specifications," Dec., 1996.

Primary Examiner—William Oen
Assistant Examiner—Maurice Stevens
Attorney, Agent, or Firm—Van Dyke, Gardner, Linn & Burkhart, LLP

[57] ABSTRACT

A method and apparatus for measuring vehicle exhaust emission includes sampling vehicle exhaust and a dilute mixture of vehicle exhaust and ambient air. A first analyzer measures concentrations of gas components of undiluted vehicle exhaust. A second analyzer measures concentration of at least one exhaust gas component present in the dilute mixture gas component. The at least one dilute mixture gas component is a particular exhaust gas component measured by the first analyzer which is also present in ambient air in substantial quantity. Flow rate of the dilute mixture, the concentration of the at least one dilute mixture gas component and undiluted gas concentration are analyzed by a microprocessor to produce mass emissions of the vehicle exhaust gas components.

33 Claims, 3 Drawing Sheets

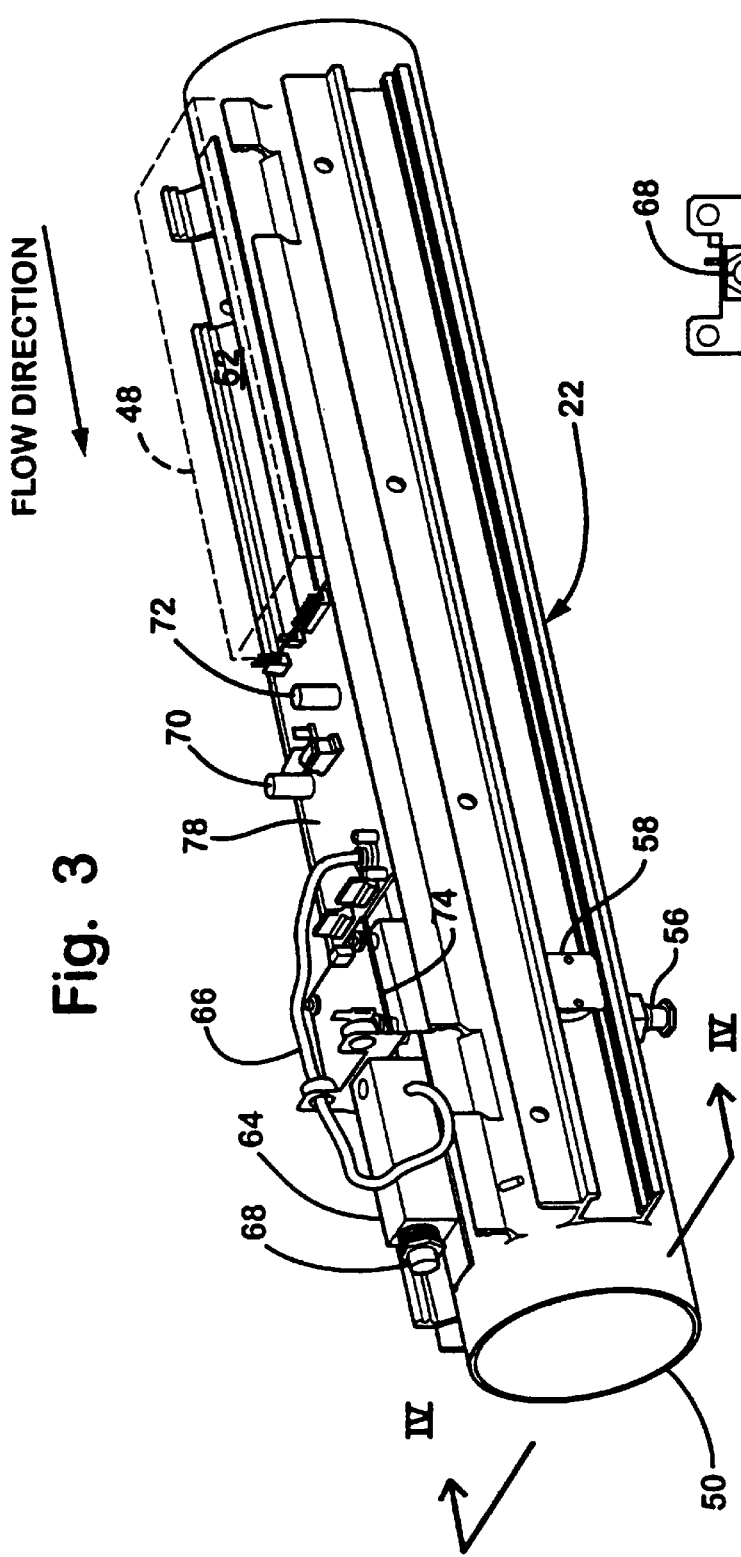

VEHICLE MASS EMISSION MEASUREMENT

CROSS-REFERENCE TO RELATED APPLICATION

This application claims priority from provisional patent application Ser. No. 60/047,192 filed on May 20, 1997.

BACKGROUND OF THE INVENTION

The present invention pertains to a method and apparatus for measuring mass emissions from a vehicle exhaust and, more particularly, to such a mass emission measurement utilizing dilution of the vehicle exhaust with air.

A vehicle exhaust emission analysis technique conventionally measures the concentrations of the component gas emissions in order to determine compliance with environmental standards. Gas concentration measurement, however, is inadequate to determine the true emissions of the vehicle. In order to measure true emissions, it is necessary to measure the mass of emissions and not just the concentration because the concentration is only one parameter of the amount of pollution generated. In order to measure mass emissions, it is necessary to also determine volume, or flow, of the exhaust gas.

One known teaching for measuring mass emission directly measures the flow of gases from the tailpipe using a technique which accounts for the operating environment. This technique is difficult to carry out because the presence of exhaust gases and high heat provides a hostile testing environment. Furthermore, an adapter must be provided which can tightly connect with a wide range of tailpipe configurations. This technique is especially difficult with dual-exhaust vehicles.

Another known technique measures concentration of exhaust gas which has been diluted. This technique requires expensive instruments because they are measuring component gas concentrations which have been diluted to very low concentrations. Furthermore, variations in exhaust gas volume causes concentration of the exhaust gases to vary, which must be taken into account in order to produce accurate results. The analyzer accuracy range must be sufficient to accommodate a low exhaust volume with a vehicle having a low pollution output as well as a high exhaust volume in a vehicle having a high pollution output. This wide sensing range adds to the expense to the instruments. Another known technique for measuring vehicle mass emission uses a carbon dioxide tracing method which determines flow rate by comparing the measured concentration of carbon dioxide in the undiluted vehicle exhaust gas with the measured concentration of carbon dioxide in a dilute mixture of exhaust gas and a diluting gas. The difficulties with such approach are two-fold. The first is that carbon dioxide is present in very low concentrations in ambient atmosphere, such as approximately 400 ppm, or 0.04%. This very low concentration of carbon dioxide in ambient air is inadequate for use in providing an accurate analyzer calibration point. When testing a vehicle, the analyzer would be operating in the single digit percent carbon dioxide range. Therefore, the use of ambient air for calibration would provide too much uncertainty at the calibration point. As a result, a source of carbon dioxide must be provided as a consumable gas in order to accurately calibrate the dilute carbon dioxide analyzer and measure dilution ratio.

The measurement of carbon dioxide in the dilute mixture of vehicle exhaust and dilution air requires filtration of the dilute mixture prior to passing the mixture over the carbon dioxide analyzer, typically a non-dispersive infrared (NDIR) analyzer, in order to remove water vapor from the dilute mixture. Such filtration requires a complicated gas-sampling system, including pumps, filters, solenoids, and the like. Without such filtration, life expectancy of the carbon dioxide sensor is reduced. However, the extra gas-sampling system adds significant cost to the analyzer. Additionally, the delay attendant to such sampling system creates a phasing between concentration measurements taken of the undiluted exhaust gas and those taken of the dilute mixture. The alignment of dilute and undiluted concentration is critical to the accuracy in the assessment of mass emissions. As the complexity of the sample system increases, the more difficult and costly it is to achieve acceptable alignment levels. As a result of cost and complexity, such technology has been practiced only in laboratory settings.

Accordingly, the need exits for a rugged, inexpensive vehicle exhaust mass emission analyzer which provides accurate measurement of vehicle mass emissions without a consumable calibration gas that can be used in laboratory and field emission testing programs.

SUMMARY OF THE INVENTION

The present invention provides a method and apparatus for measuring vehicle exhaust mass emissions which is accurate, robust, and low cost and which does not require use of a consumable calibration gas. A method of measuring vehicle exhaust mass emissions according to an aspect of the invention includes sampling undiluted vehicle exhaust and a dilute mixture of vehicle exhaust in dilution air, measuring concentration of gas components of the undiluted vehicle exhaust, measuring concentrations of a particular exhaust component of the dilute mixture, which is accurately measurable in both ambient air and vehicle exhaust, and measuring flow rate of the dilute mixture. The method further includes resolving the concentration of exhaust gas components, the concentration of the particular exhaust gas component, and the flow rate of a dilute mixture to mass emissions of the exhaust gas components. This may be accomplished using mass and volume balance equations to determine actual dilution ratio. From the actual dilution ratio and dilute mixture volume, exhaust volume can be determined. From exhaust gas volume and measured exhaust gas component concentrations, exhaust mass emissions can be accurately determined.

According to a further aspect of the invention, ambient air is sampled either prior to or after sampling exhaust gas in order to provide a calibration. In particular, this technique provides a method of calibrating the oxygen sensors using ambient air and, therefore, avoiding any additional costs associated with calibration gases.

A vehicle exhaust mass emission analyzer, according to an aspect of the invention, includes an exhaust inlet adapted to collect vehicle exhaust and a dilution air inlet connected with the exhaust inlet to provide a dilute mixture of vehicle exhaust and dilution air. A first analyzer is provided which measures concentration of exhaust gas components from the exhaust inlet. A second analyzer is provided which measures concentration of at least one dilute mixture gas component. The at least one dilute mixture gas component is a select one of the exhaust gas components which is also present in ambient air in substantial quantities. A meter is provided which measures flow rate of the dilute mixture. A processor resolves the concentration of the exhaust gas components, the concentration of the at least one dilute mixture gas component, and the flow rate of the dilute mixture to mass emissions of the exhaust gas components.

Preferably, the select one of the dilute mixture gas components which is used to determine dilution ratio is oxygen. In contrast to carbon dioxide analyzers used for dilute analyzers which require a calibration gas, expensive gas-sampling systems, and introduce phasing errors in the mass emission calculations, the measurement of oxygen in the dilute mixture can be carried out without the use of a calibration gas, an expensive gas-sampling system. This is because oxygen analyzers are available which can be exposed directly to the dilute mixture of vehicle exhaust and dilution air without substantially reducing the operating life of the sensor and the ambient air provides a calibration port at or near the operating range. Advantageously, such sensors are relatively inexpensive and accurate. This, in combination with the elimination of the calibration gas and the gas-sampling system, results in a significant reduction in the cost of the mass emission analyzer and thereby provides a more commercially useful product. Importantly, oxygen is present in sufficient quantity in ambient air to avoid the necessity for a consumable gas to accurately determine dilution ratio.

Measurement of oxygen in the dilute mixture of vehicle exhaust in dilution air is not without its difficulties. Fast-responding oxygen analyzers operate at an elevated temperature, such as 700 degrees centigrade. Such elevated temperature results in chemical reaction between oxygen and carbon monoxide and between oxygen and hydrocarbons in the dilute mixture of vehicle exhaust and dilution air. As a result, residual, or measured, dilute concentration can be less than the actual oxygen measurement for cars with varying emissions. Without compensation, such chemical reaction would adversely affect the mass emission measurement accuracy.

In order to overcome this difficulty, according to yet an additional aspect of the invention, a vehicle exhaust mass emission analyzer includes a processor which corrects the residual dilute oxygen measurement to actual oxygen measurement by compensating for the exhaust gas component available for reaction with oxygen resulting from heating of the dilute mixture by the oxygen analyzer. This may be accomplished by an iterative calculation. The iterative calculation includes: (a) calculating an initial dilution ratio of exhaust gas and dilution air ignoring any chemical reactions, (b) compensating measured concentration of oxygen as a function of the calculated initial dilution ratio and measured concentration of the time-phased exhaust gas components, and (c) resolving measured concentration of exhaust gas components and compensated concentration of oxygen to a compensated dilution ratio of time-phased exhaust gas and dilution air. This process is repeated until the solution converges according to known mathematical principles. Alternatively, a mathematical model of the interactive process may be used.

Another difficulty to be overcome by the measurement of the dilute mixture of vehicle exhaust and dilution air is the cooling effect of the dilute mixture on the oxygen analyzer. If too much heat is extracted from the oxygen analyzer, it may provide inaccurate results. In order to overcome this difficulty, according to yet an additional aspect of the invention, a flow proportionalizer may be provided to divert a portion of the diluted gas mixture to the oxygen analyzer. Because the diluted portion is significantly less than total flow of diluted gas mixture, the heat-dissipating effect may be significantly reduced.

These and other objects, advantages, and features of this invention will become apparent upon review of the following specification in conjunction with the drawings.

BRIEF DESCRIPTION OF THE DRAWINGS

FIG. 3 is a perspective view of a dilute mixture duct useful with the invention; and FIG. 4 is a view from IV—IV in FIG. 3.

DESCRIPTION OF THE PREFERRED EMBODIMENT

Figure 1:
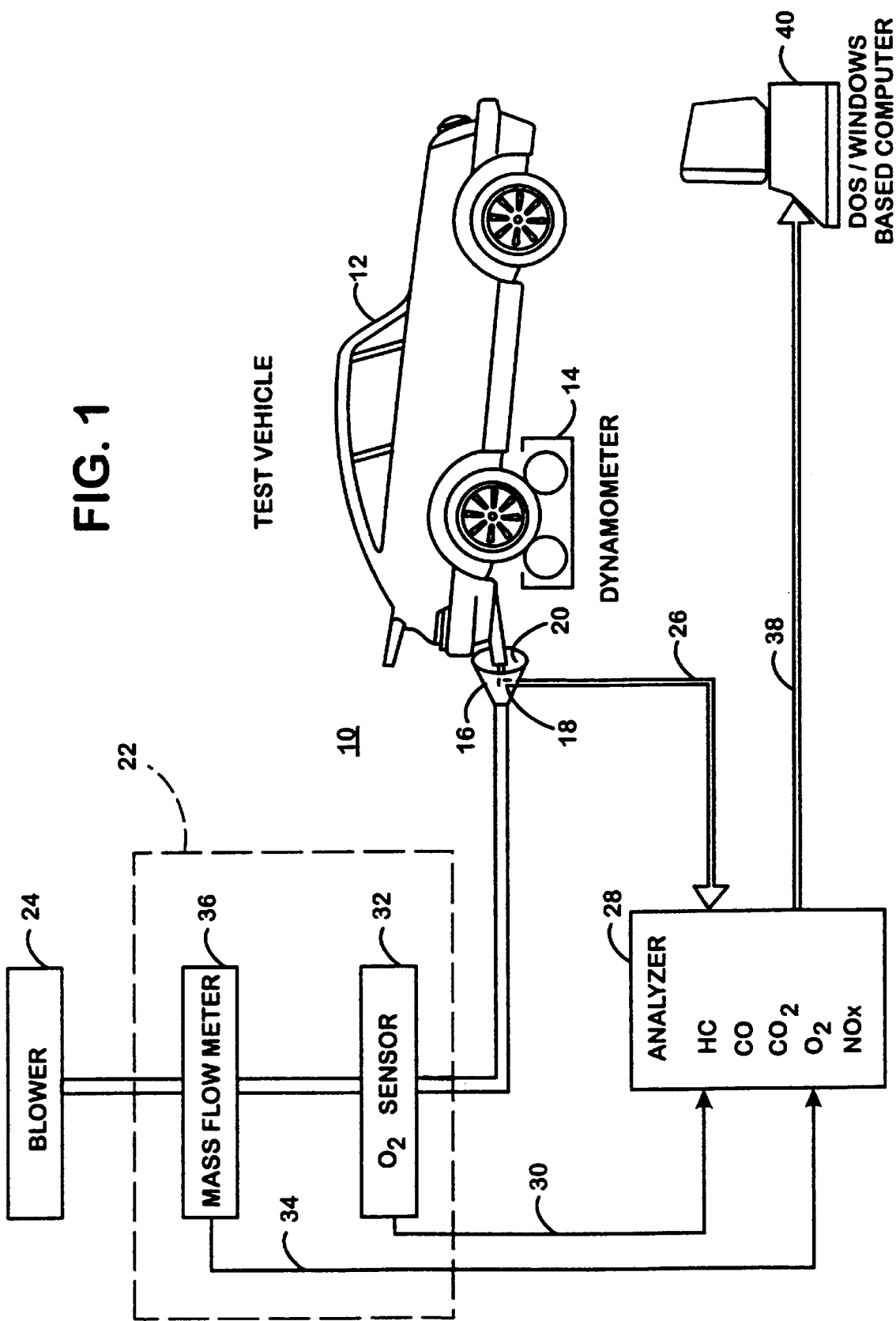
FIG. 1 is a flow diagram of a method of measuring vehicle exhaust mass emission and a vehicle exhaust mass emission analyzer, according to the invention.
Figure 2:
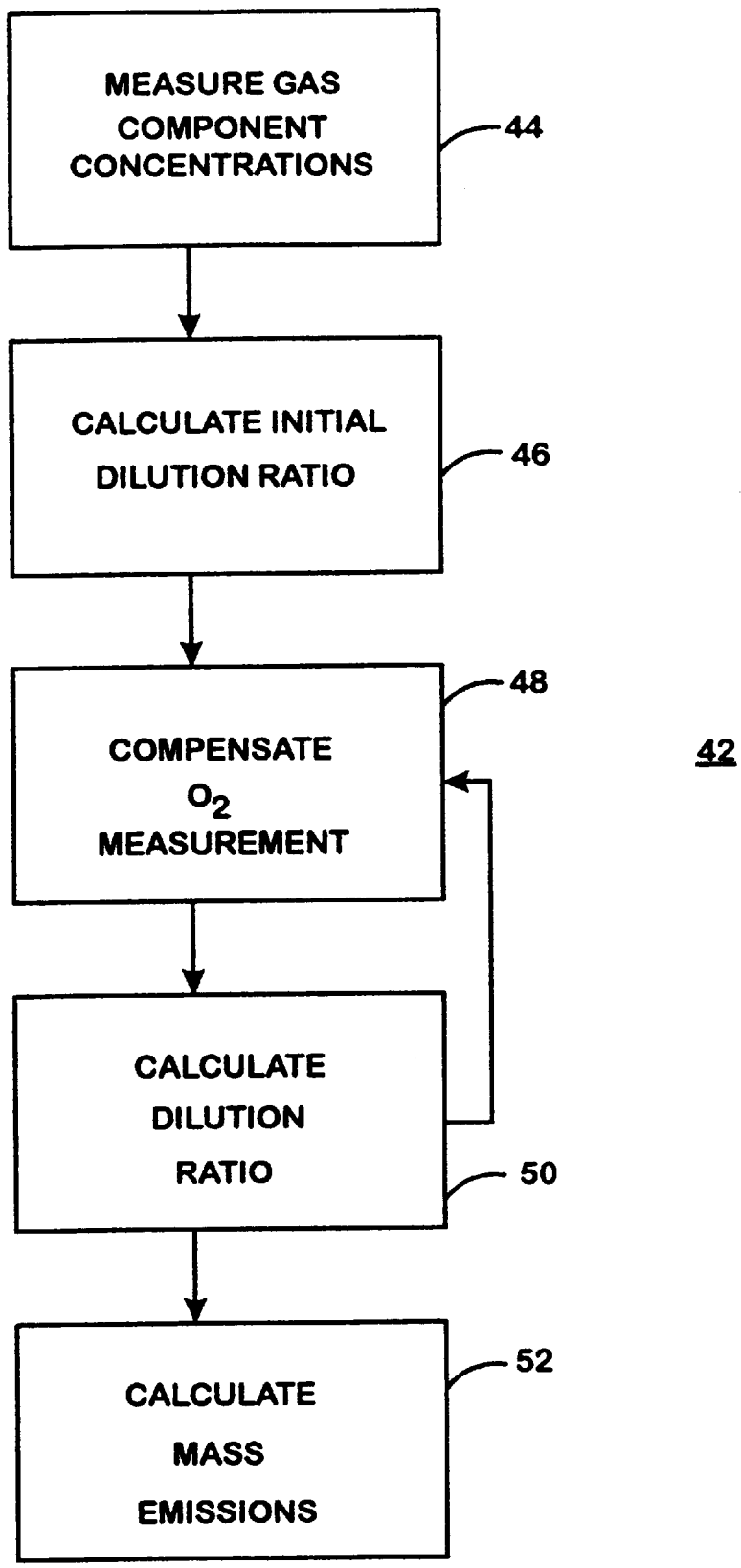
FIG. 2 is a flowchart of an iterative process for compensating for chemical interaction between oxygen and exhaust gas components.

Referring now specifically to the drawings, and the illustrative embodiments depicted therein, a vehicle exhaust mass emission analyzer and method 10 is illustrated measuring mass emissions of a vehicle 12 with the operating condition of the vehicle optionally being monitored by a dynamometer 14 (FIG. 1). A sampling assembly, or cone, 16 has an exhaust inlet 18 configured to interface with a vehicle exhaust pipe and sample undiluted exhaust gases emitted by the vehicle. Concentric with the exhaust inlet is an ambient air inlet 20 which draws ambient air from the environment outside of the vehicle. A dilute mixture duct 22 receives a diluted mixture of vehicle and exhaust dilution air induced into the duct by a blower 24.

A gas-sampling system 26 samples undiluted exhaust gas from exhaust inlet 18 and supplies gas samples to a gas concentration analyzer 28. Gas analyzer 28 measures gas concentration in the exhaust gas which may utilize principles disclosed in commonly assigned U.S. Pat. No. 5,510,269 issued to Black et al. for an INFRARED METHOD AND APPARATUS FOR MEASURING GAS CONCENTRATION INCLUDING ELECTRONIC CALIBRATION, the disclosure of which is hereby incorporated herein by reference. Analyzer 28 additionally receives an input 30 from a gas analyzer 32 which detects the concentration of a component gas in dilute mixture duct 22 as will be explained in more detail below. Preferably, gas analyzer 32 is an oxygen sensor for reasons that will be set forth in more detail below. Analyzer 28 additionally receives an input 34 from a mass flow meter 36. Mass flow meter 36 is positioned in dilute mixture duct 22, and is configured to present a low impedance on the vehicle exhaust and provides a measure of dilute mixture flow rate. Analyzer 28 includes an output 38 which is provided to a computer 40 for displaying and performing various pass/fail indications for vehicle 12 based upon mass emission measurements outputted from analyzer 28.

In order to determine mass emission of each component gas in the exhaust vehicle 12, hydrocarbon (HC), carbon monoxide (CO), carbon dioxide ($CO_2$), oxygen ($O_2$), and oxides of nitrogen ($NO_x$), it is necessary to determine both the volume of the exhaust and the concentration of each component gas. Concentration of each component gas is measured directly by analyzer 28. Exhaust gas volume $V_e$ is determined as the product of dilute mixture volume $V_d$, measured by mass flow meter 36, and a dilution ratio (d). Using this information, the mass of each component gas can be determined according to equation 1:

$$\text{Mass} = \text{Density} \times \text{Volume} \times \text{Concentration} = PVC \quad (1)$$

The mass of the dilute mixture is equal to the mass of its components for any individual or any combination of the emitted components of the exhaust gas.

$$M_d = M_e + M_a \quad (2)$$

where:

$M_d$=Mass of the diluted mixture;

$M_e$=Mass of the exhaust; and $M_a$=Mass of ambient.

Likewise, the volume of the dilute mixture is equal to the volume of its components.

$$V_d = V_e + V_a \quad (3)$$

where:
 $V_d$ is volume of dilute mixture;
 $V_e$ is volume of undiluted exhaust; and
 $V_a$ is volume of ambient.
Combining equations 2 and 3 results in:

$$P_d V_d C_d = P_e V_e C_e + P_a C_a (V_d - V_e) \quad (4)$$

where:
 $P_d$, $P_a$, and $P_e$ are the density coefficients;
 $C_d$ is measured concentration of oxygen in the dilute mixture;
 $C_a$ is measured concentration of oxygen in ambient air; and
 $C_e$ is measured concentration of oxygen in the undiluted vehicle exhaust.
Solving for volume of the exhaust results in:

$$V_e = \frac{V_d(P_d C_d - P_a C_a)}{(P_e C_e - P_a C_a)} \quad (5)$$

The value of $C_d$ is measured by oxygen analyzer 32. The value of $C_e$ is measured by analyzer 28. The value of $C_a$ may be measured by either analyzer 28 or analyzer 32, or both, when sampling assembly 16 is disconnected from the vehicle 12, such as between vehicle tests when only ambient air is being drawn in sampling assembly 16.

From the above, it can be seen that mass emissions of each of the component gases of the vehicle exhaust can be measured by the combination of analyzer 28, analyzer 32, and mass flow meter 34. In the illustrated embodiment, analyzer 32 is a zirconium oxide oxygen sensor. Such sensors are commercially available at auto parts stores and are marketed by many different manufacturers. Zirconium oxide oxygen sensors operate at an elevated temperature, such as 700 degrees centigrade. At such elevated temperatures, the oxygen in the dilute mixture of vehicle exhaust and dilution air combine with molecules of carbon monoxide and hydrocarbon, which are also present in the dilute mixture. This chemical interaction, which may include combustion, between oxygen and other component gases in the vehicle exhaust would introduce error in the mass emission calculations unless appropriate compensation is made. In order to provide compensation, a compensation algorithm 42 is performed. Compensation algorithm 42 begins by measuring gas component concentrations at 44 utilizing analyzer 32 and exhaust gas analyzer 28.

A dilution ratio is calculated ignoring the chemical reactions at 46 and utilized to compensate oxygen measurement made by analyzer 32 for reduction in oxygen molecules resulting from chemical interaction with other component gases at 48. After the measured concentration of oxygen is compensated at 48, a new dilution ratio is calculated at 50. The new dilution ratio calculated at 50 is utilized to compensate the oxygen concentration measurement at 48 and to produce a new dilution ratio at 50. This process is interactively carried out until the algorithm is determined to converge utilizing known mathematical techniques. After a dilution ratio is determined at 50, the mass emissions of the vehicle are calculated at 52. Alternatively, the iterative conveyance can be modeled and stored in a look-up table or constants in an equation.

Oxygen sensor 32 may sample dilute mixture from dilute mixture duct 22 utilizing various techniques. In one technique, the oxygen sensor is placed in the duct in order to measure oxygen directly from the air flowing through duct 22. In another embodiment, a proportionalizer system, such as a pitot tube, is utilized to sample a fixed proportion of the gas flowing through duct 22. In this embodiment, oxygen sensor 32 is placed in the portion of the diluted mixture drawn from duct 22. This embodiment is preferred because the reduced flow of dilute mixture over the oxygen sensor reduces the amount of heat dissipation caused by the dilute mixture flowing over the oxygen sensor thereby allowing the oxygen sensor to operate at its design temperature. Other sampling techniques will suggest themselves to those skilled in the art.

A detailed embodiment of dilute mixture duct 22 is illustrated in FIGS. 3 and 4 in which directing flow of dilute mixture gas is illustrated by the arrow in FIG. 3. Blower 24, which is not illustrated in FIGS. 3 and 4, would be connected at the left end of dilute mixture duct 22 as viewed in FIG. 3.

Dilution duct 22 includes a tubular housing 50 which may provide an option area 52 for mounting the sample tube assembly 48 of analyzer 28 and gas sampler 26. A vortex strut 54 is supported within housing 50 by a strut holder 56. An ultrasonic transmitter 58 and ultrasonic receiver 60 are mounted to housing 50 on opposite sides of strut 54. As will be explained in more detail below, vortex strut 54, ultrasonic transmitter 58 and ultrasonic receiver 60 in combination make up mass flow meter 36.

A gas diverter, or pitot tube 62, samples dilute mixture flowing through housing 50. The sampled gas is conveyed to an oxygen measurement chamber 64 by a tube 66. An oxygen sensor 68 is positioned in chamber 64. Pitot tube 62, oxygen measurement chamber 64, tube 66 and oxygen sensor 62 make up analyzer 32.

Dilute mixture duct 22 further includes a temperature sensor 70 and pressure sensor 72, both of which sense conditions in the interior of housing 50. A flow electronic circuit board 74, which may include a microprocessor control circuit, receives inputs from ultrasonic receiver 60 and calculates mass flow volume. A processor circuit board (not shown), which preferably includes a microprocessor control circuit, performs the analysis function of gas analyzer 28 and produces output 38.

In the illustrated embodiment, mass flow meter 36 is a flow meter system which is commercially available from J-TEC Associates of Cedar Rapids, Iowa which has been modified to meet the requirements of the present application. Mass flow meter 36 operates by transmitting an ultrasonic signal by ultrasonic transmitter 58 which is sensed by ultrasonic receiver 60. The signal passes around strut 54 and is modified by air turbulence created by the dilute mixture flowing past strut 54. The amount of turbulence created is proportional to dilute mixture flow rate. Therefore, by processing the signal received by ultrasonic receiver 60, in a manner which would be apparent to the skilled artisan, dilute mixture flow rate can be calculated.

Oxygen sensor 68 is preferably a model GMS-10 zirconium oxide sensor marketed by Philips. The oxygen sensor is preferably operated according the principles disclosed in the application guide entitled "Dynamic $ZrO_2$ oxygen sensors for improved combustion control," published by Gasmodul, a Honeywell Company, the disclosure of which is hereby incorporated herein by reference.

The present invention is both relatively inexpensive and robust in operation. This is achieved because only one gas-sampling system is required for measurement of the concentrations of the component gases of the vehicle exhaust. A separate gas-sampling system is not required for the oxygen sensor. Such oxygen sensor is readily available, inexpensive and adapted to operating in a harsh environment. Additionally, calibration of the system can be performed using ambient air. This is because oxygen comprises a large enough component of ambient air to provide a reading which is within the acceptable level of accuracy of even a moderately accurate instrument, such as, say, one percent (1%). Therefore, the requirement for a consumable calibration gas is eliminated. Importantly, the present invention provides exceptionally accurate readings of mass emissions of the vehicle irrespective of the operating conditions of the vehicle.

Changes and modifications in the specifically described embodiments can be carried out without departing from the principles of the invention, which is intended to be limited only by the scope of the appended claims, as interpreted according to the principles of patent law including the Doctrine of Equivalents.

The embodiments of the invention in which an exclusive property or privilege is claimed are defined as follows:

1. A vehicle exhaust mass emission analyzer, comprising:
   an exhaust inlet adapted to collect vehicle exhaust;
   a dilution air inlet connected with said exhaust inlet to provide a dilute mixture of vehicle exhaust and dilution air;
   a first analyzer which measures concentration of undiluted exhaust gas components from said exhaust inlet;
   a second analyzer which measures concentration of at least one dilute mixture gas component, said at least one dilute mixture gas component being a particular exhaust gas component measured by said first analyzer which is also present in ambient air in an accurately measurable quantity;
   a meter which measures flow rate of said dilute mixture; and
   a processor which computes mass of the exhaust gas components from said concentration of the undiluted exhaust gas components, said concentration of at least one dilute mixture gas component and said flow rate of said dilute mixture.

2. The vehicle exhaust mass emission analyzer in claim 1 wherein said second analyzer comprises an oxygen analyzer.

3. The vehicle exhaust mass emission analyzer in claim 2 wherein said oxygen analyzer comprises a heated zirconium-oxide medium.

4. The vehicle exhaust mass emission analyzer in claim 3 wherein said processor compensates the mass of exhaust gas components for chemical reaction of said at least one dilute mixture gas component and said exhaust gas components.

5. The vehicle exhaust mass emission analyzer in claim 4 wherein said chemical reaction results at least in part from heating of said dilute mixture by said oxygen analyzer.

6. The vehicle exhaust mass emission analyzer in claim 4 wherein said processor compensates the mass of exhaust gas components by an iterative calculation or model.

7. The vehicle exhaust mass emission analyzer in claim 4 wherein said processor compensates the mass of exhaust gas components by: (a) calculating an initial dilution ratio of exhaust gas and dilution air, (b) compensating measured concentration of said at least one dilute mixture gas component as a function of said initial dilution ratio and measured concentration of undiluted exhaust gas components, (c) resolving measured concentration of undiluted exhaust gas components and compensated concentration of said at least one dilute mixture gas component to compensated dilution ratio of exhaust gas and dilution air.

8. The vehicle exhaust mass emission analyzer in claim 7 including repeating steps (b) and (c).

9. The vehicle mass emission analyzer in claim 1 wherein said processor compensates the mass of exhaust gas components for chemical reaction of said at least one dilute mixture gas component and said exhaust gas components.

10. The vehicle exhaust mass emission analyzer in claim 1 including a flow proportionalizer to divert a portion of the dilute gas mixture wherein said second gas analyzer measures said concentration of said particular one dilute gas component in the diverted portion of dilute gas mixture.

11. The vehicle exhaust mass emission analyzer in claim 10 wherein said second analyzer comprises an oxygen analyzer which is heated above dilute mixture temperature.

12. The vehicle exhaust mass emission analyzer in claim 1 including a blower for propelling dilute mixture of exhaust and dilution air.

13. The vehicle exhaust mass emission analyzer in claim 1 wherein said processor resolves the concentration of undiluted exhaust gas components, the concentration of at least one dilute mixture gas component and the flow rate of said dilute mixture to the mass of said exhaust gas components using the formula:

$$V_e = V_d \frac{(P_d C_d - P_a C_a)}{(P_e C_e - P_a C_a)}$$

where:
   $V_e$ is volume of the exhaust;
   $V_d$ is volume of the dilute mixture;
   $P_d$, $P_a$, and $P_e$ are the density coefficients of the dilute mixture, ambient air, and exhaust gas, respectively;
   $C_d$ is measured concentration of the at least one dilute mixture gas component in the dilute mixture;
   $C_a$ is measured concentration of the at least one dilute mixture gas component in ambient air; and
   $C_e$ is measured concentration of the at least one dilute mixture gas component undiluted in the vehicle exhaust.

14. A vehicle exhaust mass emission analyzer, comprising:
   an exhaust inlet adapted to collect vehicle exhaust;
   a dilution air inlet connected with said exhaust inlet to provide a dilute mixture of exhaust and dilution air;
   a first analyzer which measures concentration of undiluted exhaust gas components from said exhaust inlet;
   a second analyzer which measures concentration of at least one dilute mixture gas component, said at least one dilute mixture gas component being a particular said exhaust gas component also measured by said first analyzer;
   a meter which measures flow rate of said dilute mixture; and
   a processor which calculates mass of the exhaust gas components from the concentration of undiluted exhaust gas components, the concentration of at least one dilute mixture gas component and the flow rate of said dilute mixture, wherein said processor compensates mass of exhaust gas components for chemical reaction of said at least one dilute mixture gas component and said exhaust gas components.

15. The vehicle exhaust mass emission analyzer in claim 14 wherein said chemical reaction results at least in part from heating of said dilute mixture by said second analyzer.

16. The vehicle exhaust mass emission analyzer in claim 14 wherein said processor compensates the mass emissions of exhaust gas components by an iterative calculation.

17. The vehicle exhaust mass emission analyzer in claim 14 wherein said processor compensates the mass emissions of exhaust gas components by: (a) calculating an initial dilution ratio of exhaust gas and dilution air, (b) compensating measured concentration of said at least one dilute mixture gas component as a function of said initial dilution ratio and measured concentration of undiluted exhaust gas components, (c) resolving measured concentration of undiluted exhaust gas components and compensated concentration of said at least one dilute mixture gas component to compensated dilution ratio of exhaust gas and dilution air.

18. The vehicle exhaust mass emission analyzer in claim 17 wherein said processor repeats steps (b) and (c).

19. The vehicle exhaust mass emission analyzer in claim 14 including a flow proportionalizer to divert a portion of the dilute gas mixture wherein said second gas analyzer measures the concentration of said at least one dilute gas component in the diverted portion of dilute gas mixture.

20. The vehicle exhaust mass emission analyzer in claim 14 including a blower for propelling dilute mixture of exhaust and dilution air.

21. The vehicle exhaust mass emission analyzer in claim 14 wherein said processor resolves the concentration of undiluted exhaust gas components, the concentration of at least one dilute mixture gas component and the flow rate of said dilute mixture to the mass of said exhaust gas components using the formula:

$$V_e = V_d \frac{(P_d C_d - P_a C_a)}{(P_e C_e - P_a C_a)}$$

where:

$V_e$ is volume of the exhaust;

$V_d$ is volume of the dilute mixture;

$P_d$, $P_a$, and $P_e$ are the density coefficients of the dilute mixture, ambient air, and exhaust gas, respectively;

$C_d$ is measured concentration of the at least one dilute mixture gas component in the dilute mixture;

$C_a$ is measured concentration of the at least one dilute mixture gas component in ambient air; and $C_e$ is measured concentration of the at least one dilute mixture gas component undiluted in the vehicle exhaust.

22. The vehicle exhaust emission analyzer in claim 14 wherein said second analyzer is an oxygen analyzer.

23. A method of measuring vehicle exhaust mass emission, comprising:

sampling undiluted vehicle exhaust and a dilute mixture of vehicle exhaust and ambient air;

measuring concentrations of undiluted gas components of said vehicle exhaust;

measuring concentration of at least one dilute mixture gas component, the at least one dilute mixture gas component being a particular exhaust gas component which is accurately measurable in ambient air;

measuring flow rate of said dilute mixture; and calculating mass emissions of the exhaust gas components from said concentration of undiluted exhaust gas components, said concentration of said particular component and said flow rate of said dilute mixture.

24. The method of claim 23 including sampling only ambient air in order to provide a calibration before or after said sampling.

25. The method of claim 23 wherein said particular exhaust gas component is oxygen.

26. The method of claim 25 wherein said resolving includes compensating measured oxygen for chemical reaction of oxygen and the exhaust gas components.

27. The method of claim 26 wherein said measuring concentration in said dilute mixture comprises using a heated zirconium-oxide medium.

28. The method of claim 27 wherein said chemical reaction results at least in part from heating of the dilute mixture.

29. The method of claim 27 wherein said compensating comprises performing an iterative calculation.

30. The method of claim 26 wherein said compensating includes: (a) assuming an estimated dilution ratio of exhaust gas and dilution air, (b) compensating measured concentration of oxygen in said dilute mixture as a function of said estimated dilution ratio and measured concentration of undiluted exhaust gas components, and (c) resolving measured concentration of undiluted exhaust gas components and compensated concentration of oxygen in said dilute mixture to compensated dilution ratio of exhaust gas and dilution air.

31. The method of claim 30 including repeating steps (b) and (c).

32. The method of claim 23 wherein said resolving includes compensating said particular gas component for chemical reaction of said particular component and said exhaust gas components.

33. The method of claim 23 wherein said resolving said concentration of undiluted exhaust gas components, the concentration of said particular gas component and the flow rate of said dilute mixture to the mass of said exhaust gas components includes:

$$V_e = V_d \frac{(P_d C_d - P_a C_a)}{(P_e C_e - P_a C_a)}$$

where:

$V_e$ is volume of the exhaust;

$V_d$ is volume of the dilute mixture;

$P_d$, $P_a$, and $P_e$ are the density coefficients of the dilute mixture, ambient air, and exhaust gas, respectively;

$C_d$ is measured concentration of oxygen in the dilute mixture of the gas component present in both ambient air and vehicle exhaust;

$C_a$ is measured concentration of ambient air of the gas component present in both ambient air and vehicle exhaust; and $C_e$ is measured concentration in the vehicle exhaust of the gas component present in both ambient air and undiluted vehicle exhaust.

* * * * *